United States Patent [19]

Tari et al.

[11] Patent Number: 5,417,978
[45] Date of Patent: May 23, 1995

[54] LIPOSOMAL ANTISENSE METHYL PHOSPHONATE OLIGONUCLEOTIDES AND METHODS FOR THEIR PREPARATION AND USE

[75] Inventors: Ana Maria Tari; Gabriel Lopez-Berestein; Albert B. Deisseroth, all of Houston, Tex.

[73] Assignee: Board of Regents, The University of Texas System, Austin, Tex.

[21] Appl. No.: 99,229

[22] Filed: Jul. 29, 1993

[51] Int. Cl.$^6$ .............................................. A61K 37/22
[52] U.S. Cl. ..................................... 424/450; 514/44; 536/24.1
[58] Field of Search ........................... 424/450; 514/44; 536/24.1

[56] References Cited

U.S. PATENT DOCUMENTS

| | | | |
|---|---|---|---|
| 4,721,612 | 1/1988 | Janoff et al. | 424/1.1 |
| 4,950,432 | 8/1990 | Mehta et al. | 264/4.6 |
| 5,030,442 | 7/1991 | Uster et al. | 424/45 |
| 5,049,388 | 9/1991 | Knight et al. | 424/450 |
| 5,087,617 | 2/1992 | Smith | 514/44 |
| 5,098,890 | 3/1992 | Gewirtz et al. | 514/44 |
| 5,100,662 | 3/1992 | Bolcsak et al. | 424/88 |
| 5,112,962 | 5/1992 | Letsinger et al. | 536/27 |
| 5,135,917 | 8/1992 | Burch | 514/44 |
| 5,178,875 | 1/1993 | Lenk et al. | 424/450 |

FOREIGN PATENT DOCUMENTS

WO89/06977 8/1989 WIPO.
WO90/90180 8/1990 WIPO.

OTHER PUBLICATIONS

Akhtar et al., "Interactions of Antisense DNA Oligonucleotide Analogs with Phospholipid Membranes (Liposomes)", Nucleic Acids Research, 19:20, pp. 5551–5559 (Sep. 16, 1991).
Thierry et al., "Liposomal Delivery as a New Approach to Transport Antisense Oligonucleotides", Gene Regulation: Biology of Antisense RNA and DNA, 1:147–161 (1992).
Wickstrom, "Antisense DNA Therapeutics: Neutral Analogs and Their Stereo–chemistry", Raven Press Ser. Mol. Cell. Biol. 1:119–132 (1992) [CA:117(7) 63817b].
Thierry et al., "Intracellular Availability of Unmodified Phosphorothioated and Liposomally Encapsulated Oligodeoxynucleotides for Antisense Activity", Nucleic Acids Research, 20:21, pp. 5691–5698 (Sep. 28, 1992).
Yeoman et al., "Lipofectin Enhances Cellular Uptake of Antisense DNA While Inhibiting Tumor Cell Growth", Antisense Research and Development 2:51–59 (1992).
Juliano et al., "Liposomes as a Drug Delivery System for Antisense Oligonucleotides", Antisense Research and Development 2:165–176 (1992).
Akhtar et al., "Release of Antisense Oligodeoxynucleotide Analogues From Liposomes: Implications for Cellular Transport and Drug Delivery", 128th Meeting of British Pharmaceutical Conference 1991, Uk, (List continued on next page.)

Primary Examiner—Nathan M. Nutter
Attorney, Agent, or Firm—Arnold, White & Durkee

[57] ABSTRACT

A liposomal methyl phosphonate oligonucleotide composition useful in treatment of chronic myeloid leukemia comprises (a) a liposome which comprises at least one phospholipid, and (b) an antisense methyl phosphonate oligonucleotide which is entrapped in the liposome. The molar ratio of phospholipid in the liposome to the methyl phosphonate entrapped in the liposome is between about 100:1 and about 10,000:1. A process for making the composition includes the steps of (a) mixing an antisense methyl phosphonate oligonucleotide in a first organic solvent with at least one phospholipid in a second organic solvent, where the molar ratio of phospholipid to methyl phosphonate is between about 100:1 and about 10,000:1, (b) lyophilizing the mixture formed in step (a), producing a lyophilized powder, (c) hydrating the lyophilized powder, and (d) sonicating the hydrated material.

10 Claims, 2 Drawing Sheets

OTHER PUBLICATIONS

9/10–13/91, J. Pharm. Pharmacol. 43 (Suppl.) 1991, abstract 24 P.

Thierry et al., "Modulation of Multidrug Resistance by Antisense Oligonucleotides Encapsulated in Liposomes", Proceedings of the American Association for Cancer Research, 32:2578, p. 433 (Mar. 1991).

Miller, "Oligonucleoside Methylphosphonates as Antisense Reagents", Bio/Technology, 9:358–362 (Apr. 1991).

Boiziau et al., "Modified Oligonucleotides in Rabbit Reticulocytes: Uptake, Stability and Antisense Properties", Biochimie 73:11, pp. 1403–1408 (Nov. 1991).

Renneisen et al., "Inhibition of Expression of Human Immunodeficiency Virus-1 in Vitro by Antibody-targeted Liposomes Containing Antisense RNA to the env Region", The Journal of Biological Chemistry, 265:27, pp. 16337–16342 (Sep. 25, 1990).

Leonetti et al., "Antibody-targeted Liposomes Containing Oligodeoxyribonucleotides Complementary to Viral RNA Selectively Inhibit Viral Replication", Proc. Natl. Acad. Sci. USA, 87:7, pp. 2448–2451 (Apr. 1990).

Vasanthakumar et al., "Modulation of Drug Resistance in a Daunorubicin Resistant Subline with Oligonucleoside Methylphosphonates", Cancer Communications, 1:4, pp. 225–232 (1989).

Tidd et al., "Partial Protection of Oncogene, Anti-sense Oligodeoxy-nucleotides Against Serum Nuclease Degradation Using Terminal Methyl-phosphonate Groups", Be. S. Cancer, 60:343–350 (1989).

Moody et al., "Regiospecific Inhibition of DNA Duplication by Antisense Phosphate-Methylated Oligodeoxynucleotides", Nucleic Acids Research, 17:12, pp. 4769–4782 (May 15, 1989).

Loke et al., "Delivery of C-MYC Antisense Oligodeoxynucleotides to Hematopoietic Cells in Culture by Liposome Fusion: Specific Reduction in C-MYC Protein Expression Correlates with Inhibition of Cell Growth and DNA Synthesis", Clinical Research: AFCR Immunology, 36:3, p. 443A (1988).

Tidd et al., "Evaluation of N-ras Oncogene Anti-sense, Sense and Nonsense Sequence Methylphosphonate Oligonucleotide Analogues", Anti-Cancer Drug Design, 3:117–127 (Apr. 26, 1988).

Loke et al., "Delivery of c-myc Antisense Phosphorothioate Oligodeoxy-nucleotides to Hematopoietic Cells in Culture by Liposome Fusion: Specific Reduction in c-myc Protein Expression Correlates with Inhibiton of Cell Growth and DNA Synthesis", Current Topics in Microbiology, 141: 282–289 (1988).

Stein et al., "Oligodeoxynucleotides as Inhibitors of Gene Expression: A Review", Cancer Research, 48:10, pp. 2659–2668 (May 15, 1988).

Tsuchida et al., "Iron-Ligand Bonding Properties of Synthetic Iron-Porphyrin Complexes with Oxygen Transporting Ability in Aqueous Media", J. Chem. Soc., 10:2455–2458 (Oct. 1987).

Arad et al., "Use of Reconstituted Sendai Virus Envelopes for Fusion-Mediated Microinjection of Double-Stranded RNA: Inhibition of Protein Synthesis in Interferon-Treated Cells", Biochimica et Biophysica Acta, 859:88–94, (1986).

Agris et al., "Inhibition of Vesicular Stomatitis Virus Protein Synthesis Infection by Sequence-Specific Oligodeoxyribonucleoside Methylphosphonates", Biochemistry, 25:6268–6275 (1986).

Skorski et al., "Gene-targeted Specific Inhibition of Chronic Myeloid Leukemia Cell Growth by BCR-ABL Antisense Oligodeoxynucleotides", Folia Histochemica et Cytobiologica, 29:3, pp. 85–90 (1991).

Martiat et al., "Retrovirally Transduced Antisense Sequences Stably Suppress P210$^{BCR-ABL}$ Expression and Inhibit the Proliferation of BCR/ABL–Containing Cell Lines", Blood, 81:2, pp. 502–509 (Jan. 15, 1993).

Taj et al., "Inhibition of P210$^{BCR/ABL}$ Expression in K562 Cells by Electroporation With an Antisense Oligonucleotide", ? and Lymphoma, 3:201–208 (May 19, 1990).

Szczylik et al., "Selective Inhibition of Leukemia Cell Proliferatioin by BCR-ABL Antisense Oligodeoxynucleotides", Science, 253:562–565 (May 7, 1991).

LIPOSOMAL ANTISENSE METHYL PHOSPHONATE OLIGONUCLEOTIDES AND METHODS FOR THEIR PREPARATION AND USE

BACKGROUND OF THE INVENTION

The present invention relates to liposomal formulations of antisense oligonucleotides, methods of making such formulations, and methods of using them to treat cancer.

Chronic myeloid leukemia (CML) is an acquired clonal disorder involving the hematopoietic stem cell characterized by a prominent expansion of granulocytes. 90-95% of CML patients have a Philadelphia chromosome (Ph+) in the dividing bone marrow cells. The Ph+ chromosome results from a reciprocal translocation, t(9;22) (q34;q11), which relocates the c-abl protooncogene on chromosome 9 to the breakpoint cluster region (bcr) of chromosome 22. The bcr-abl hybrid gene encodes a novel $p210^{bcr-abl}$ fusion protein with tyrosine kinase activity. $p210^{bcr-abl}$ is of either L-6 (bcr exon II and c-abl exon "2" linkage or b2/a2 linkage) or K-28 linkage (bcr exon II and c-abl exon "2" linkage or b3/a2 linkage). $p210^{bcr-abl}$ is believed to be involved in the pathogenesis of the disease by promoting selectively the expansion of mature myeloid progenitor cells.

The disease divides into two clinical phases: an initial chronic phase, followed by a fatal blast crisis phase. The treatment of CML is very problematic. The established methods of treatment of CML are (1) interferon and (2) syngeneic or allogeneic bone marrow transplant. Only 25% of patients develop long-term remissions. Goldman and Calabretta found that antisense oligonucleotides directed to the translation initiation site of the bcr-abl mRNA induced a reduction of $p210^{bcr-abl}$ expression and suppressed the growth of Ph+ cells but not Ph− cells. Thus the use of antisense oligonucleotides may offer a new therapeutic approach to CML.

The two main obstacles in using antisense oligonucleotides to inhibit gene expression are: (a) cellular instability and (b) cellular uptake. Natural phosphodiesters are not resistant to nuclease hydrolysis; thus high concentrations of antisense oligonucleotides are needed before any inhibition effect is observed. Modified phosphodiester analogs, such as phosphorothioates and methyl phosphonates, have been made to overcome this nuclease hydrolysis problem, but they have not provided a completely satisfactory solution to the problem.

The cellular uptake of antisense oligonucleotides is low. To solve this problem, two different approaches have been used. One approach is to use high concentrations of antisense oligonucleotides. Even though this approach can increase the uptake of antisense oligonucleotides, it may also induce non-specific, toxic side effects. The other approach is to use physical techniques such as calcium-phosphate precipitation, DEAE-dextran mediation, or electroporation to increase the cellular uptake of oligos. These techniques are difficult to reproduce and are inapplicable in vivo.

There is a need for improved antisense compositions for use in treatment of disease, and also a need for processes for making such improved compositions.

SUMMARY OF THE INVENTION

The present invention relates to a liposomal methyl phosphonate oligonucleotide composition. The composition comprises (a) a liposome which comprises at least one phospholipid, and (b) an antisense methyl phosphonate oligonucleotide which is entrapped in the liposome. The molar ratio of phospholipids in the liposome to the methyl phosphonate entrapped in the liposome is between about 100:1 and about 10,000:1.

"Entrap" and "incorporate" are used in this patent to mean that the antisense methyl phosphonate oligonucleotide is enclosed within a lipid vesicle or is otherwise contained somewhere within the walls of a liposome.

In preferred embodiments of the invention, the at least one phospholipid is selected from the group consisting of phosphatidyl cholines and phosphatidyl serines, with dioleoyl phosphatidyl choline being a particularly preferred lipid. The molar ratio of phospholipids in the liposome to the methyl phosphonate oligonucleotide entrapped in the liposome is preferably between about 500:1 and about 5,000:1, most preferably about 1,000:1. The liposome is preferably unilamellar.

The present invention also relates to a process for making a liposomal methyl phosphonate nucleotide composition. The process includes the steps of (a) mixing an antisense methyl phosphonate oligonucleotide in a first organic solvent with at least one phospholipid in a second organic solvent, where the molar ratio of phospholipid to methyl phosphonate is between about 100:1 and about 10,000:1, (b) lyophilizing the mixture formed in step (a), thereby producing a lyophilized powder, (c) hydrating the lyophilized powder, and (d) sonicating the hydrated material.

The lyophilized powder is preferably hydrated in step (c) to a concentration between about 5 mM and about 50 mM, most preferably to a concentration of about 10 mM. The first organic solvent is preferably dimethyl sulfoxide and the second organic solvent is preferably t-butanol, with t-butanol being used in excess such that the concentration of t-butanol in the mixture of step (a) is at least 95% by volume.

The present invention also relates to a method of treating chronic myeloid leukemia, comprising administering to a living mammalian subject in an amount effective to inhibit the growth of leukemic cells an antisense liposomal methyl phosphonate oligonucleotide composition as described above. The composition should also be useful in the treatment of other disease conditions in which similar gene rearrangements are observed, including cancers of a number of types, such as cancers of the cells of the hemopoietic system.

The advantages of the invention include improved stability of the antisense oligonucleotides compositions under biologic conditions, improved uptake of the composition in cells, improved incorporation efficiency of the oligonucleotides into liposomes, and enhanced specific therapeutic effect of the antisense oligonucleotides against CML and other disease conditions in which similar gene rearrangements are observed.

DETAILED DESCRIPTION OF SPECIFIC EMBODIMENTS

Figure 1:
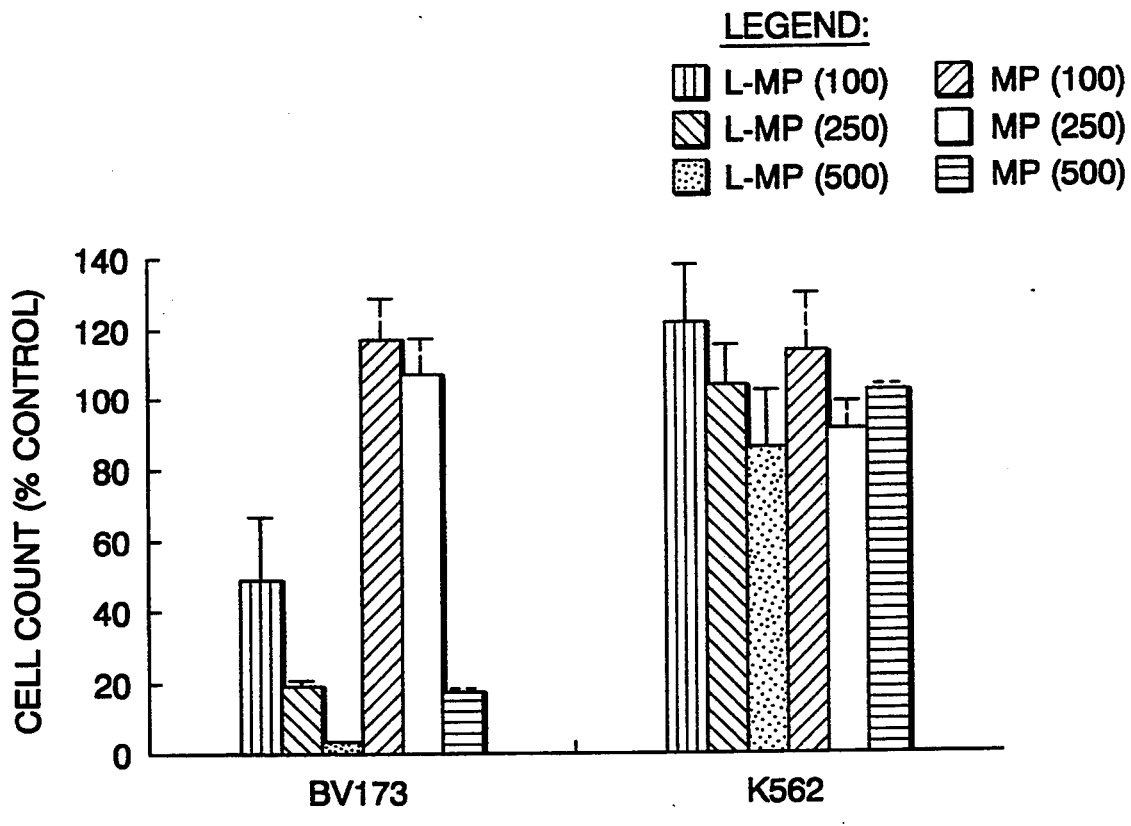
FIG. 1 shows growth inhibition of BV 173 and K562 cells by liposomal or free methyl phosphonate complementary to the L6 junction of the bcr-abl fusion gene mRNA. Concentrations of liposomal or free MP used varied between 100 to 500 nM. After 5 days of treatment, the cells were harvested over a 10% Ficoll solution and counted. The number of treated cells were reported as percent of the number of untreated cells. The values were reported as an average of two wells±error.

For optimal therapeutic use, antisense oligonucleotides have to be resistant to nuclease hydrolysis and yet retain the full capacity to form hydrogen bonds with the target mRNA bases. The present invention achieves those goals, in part through the use of methyl phosphonate derivatives of antisense oligonucleotides. Methyl phosphonates are phosphodiester analogs that have substituted a methyl group at the nonbridging oxygen atom in the phosphate backbone. This structural modification makes the methyl phosphonate oligonucleotide a non-ionic analog. Thus it is insoluble in aqueous solutions and can only be dissolved in organic solvents.

The cellular uptake of methyl phosphonates is believed to be passive diffusion, which is a slow and limiting process. Therefore, the present invention uses liposomes as a carrier to avoid the limitations of the passive diffusion mechanism and to avoid the usage of organic solvents.

"Liposomes" is used in this patent to mean lipid-containing vesicles having a lipid bilayer, as well as other lipid carrier particles which can entrap antisense oligonucleotides. The liposomes can be made of one or more phospholipids, optionally including other materials such as sterols. Suitable phospholipids include phosphatidyl cholines, phosphatidyl serines, and many others that are well known in this field. The liposomes can be, for example, multilamellar or have an undefined lamellar structure, but are preferably unilamellar.

The techniques of the present invention are believed useful with all antisense methyl phosphonate oligonucleotides. The methyl phosphonate oligos used in the examples in this patent have between 16-18 bases.

A liposomal composition in accordance with the present invention can be made by, for example, dissolving methyl phosphonate oligonucleotides with a first organic solvent. The first organic solvent preferably will be a mixture of organic solvents and water, but preferably contains at least one of dimethyl sulfoxide (DMSO) or acetonitrile. Phospholipids (and optionally other materials such as sterols) are provided in a second organic solvent. The second organic solvent can also be a mixture of organic solvents and water, but preferably contains tertiary butanol. The oligonucleotides and phospholipids together with their solvents are mixed, preferably in the presence of an excess of t-butanol so that the final volume of t-butanol in the mixture will be at least 95%. The mixture can then be agitated, for example by being vortexed, and then frozen in, for example, an acetone/dry ice bath. The frozen mixture is then lyophilized and subsequently hydrated, for example with a saline solution. The liposomes that are formed are preferably sonicated.

The liposomal composition could also be prepared by other processes.

A composition of the present invention is preferably administered to a patient parenterally, for example by intravenous, intraarterial, intramuscular, intralymphatic, intraperitoneal, subcutaneous, intrapleural, or intrathecal injection, or may be used in ex vivo bone marrow purging. Preferred dosages are between 0.01-1.0 g/kg. The administration is preferably repeated on a timed schedule until the cancer disappears or regresses, and may be in conjunction with other forms of therapy.

The making and use of the present invention is further illustrated by the following example.

Materials

Methyl phosphonate oligonucleotides were synthesized by Genta, Inc. Phospholipids were purchased from Avanti Polar Lipids.

Oligonucleotide Labeling

Methyl phosphonate oligonucleotides (MP), synthesized with a phosphodiester base at the 5' end, were labeled at 37° C. with [$^{32}$P$\gamma$]ATP at the 5' end by T4 kinase. The MP labeling reaction was carried out for 24 h. The oligonucleotide as precipitated with ethanol at −20° C. overnight. After washing with 70% ethanol three times, MP oligonucleotides were twice filtered with a Microcon-3 filter to separate the labeled oligonucleotide from free [$^{32}$P$\gamma$]ATP.

Liposome Preparation

Methyl phosphonates oligonucleotides dissolved in DMSO were mixed with phospholipids in the presence of excess t-butanol so that the final volume of t-butanol in the mixture was at least 95%. Trace amounts of [$^{3}$H]cholestanyl ether and [$^{32}$P]MP were also added to the mixture as lipid and oligonucleotide markers, respectively. The mixture was vortexed before being frozen in an acetone/dry ice bath. The frozen mixture was lyophilized and hydrated with Hepes buffered saline (1 mM Hepes and 10 mM NaCl) overnight. Liposomes were twice sonicated for 10 min in a bath type sonicator. Empty liposomes were prepared in a similar manner, except that no oligonucleotide was added to the lipids before the freezing process.

Separation of Free Oligonucleotides From Those Incorporated in Liposomes

The separation of free MP from MP incorporated in liposomes was done by loading the mixture over a 10% Ficoll solution, which was centrifuged for 10 min at 2000 rpm. Aliquots of the preparation were taken before and after centrifugation for liquid scintillation counting to assess the incorporation of MP in liposomes. Typically, MP was incorporated into liposomes with a 90% or greater efficiency.

Delivery of Oligonucleotides to Cells

Fifty thousand cells/well were seeded in a 24-well plate in 1 ml of media. After 2 h of seeding, final concentrations of 100-500 nM of oligos were added to cells either as liposomal oligonucleotides or free oligonucleotides. After 5 days of delivery, cells were harvested over a 10% Ficoll solution. The number of cells was then counted by a Coulter counter.

Before the incorporation of MP into liposomes, it was important to find an efficient method to remove the viscous DMSO efficiently, because any traces of organic solvent such as DMSO could prevent the formation of liposomes. Two different techniques of removing DMSO were used: rotoevaporation and lyophilization. It was found that lyophilization can successfully remove DMSO efficiently and quickly, whereas rotoevaporation cannot. However since DMSO has a low freezing point, an excess amount of t-butanol was added to enhance the freezing process. The final volume of t-butanol should be at least 95% of the total mixture.

The lipid phosphatidylcholine (PC) was chosen for the incorporation of MP because (1) both PC and MP are neutral molecules, so they should be compatible and (2) PC is well-studied lipid and is easy to handle. To incorporate MP into liposomes, MP was mixed with dioleoyl phosphatidyl choline (DOPC) in the presence of an excess of t-butanol before the freezing and the lyophilization processes. Various molar ratios of DOPC to MP were used. When DOPC/MP multilamellar vesicles were prepared, MP was successfully incorporated in DOPC liposomes but only with less than 15% efficiency (Table 1). The incorporation efficiency was dependent on the molar ratio of DOPC to MP. The greatest efficiency of incorporation was observed when the molar ratio of DOPC to MP was 1000:1.

TABLE 1

Effect of molar ratio of DOPC to MP on the incorporation of MP in multilamellar vesicles.

| Molar ratio of DOPC:MP | Incorporation efficiency (%)[a] |
|---|---|
| 10:1 | 0 |
| 100:1 | 0 |
| 500:1 | 6.4 |
| 1000:1 | 13.8 |
| 10000:1 | 2.6 |

[a]The incorporation efficiency values were obtained from one experiment.

Various techniques of preparing the DOPC/MP liposomes were studied. Table 2 shows that the efficiency of incorporation of MP in DOPC liposomes was much higher ($\approx 88\%$) when the liposomes were sonicated.

TABLE 2

Effect of sonication on the incorporation of MP in DOPC liposomes.

| Methods of Liposome Preparation[a] | Incorporation efficiency (%)[b] |
|---|---|
| Unsonicated multilamellar vesicles | 17 |
| Unsonicated extruded unilamellar vesicles | 15 |
| Sonicated unilamellar vesicles | 88 |

[a]The molar ratio of DOPC to MP was 1000:1.
[b]The incorporation efficiency values were obtained from one experiment.

Sonicated, unilamellar DOPC-containing liposomes were prepared to incorporate MP. The technique was identical in all cases. However, the molar ratios of DOPC to MP were varied. Table 3 shows that the incorporation efficiency of MP was dependent on the molar ratio of DOPC to MP.

TABLE 3

Effect of molar ratio of DOPC to MP on the incorporation efficiency of MP in sonicated, unilamellar liposomes.

| Molar ratio of DOPC:MP | Incorporation efficiency (%)[a] |
|---|---|
| 10:1 | 13.7 |
| 100:1 | 13.2 |
| 1000:1 | 77.4 |
| 10000:1 | 28.1 |

[a]The incorporation efficiency values were obtained from one experiment.

Similar to the multilamellar vesicles, the highest incorporation efficiency was observed when DOPC to MP was at a 1,000:1 molar ratio.

The lipid composition was varied as well as the final hydration concentration of liposomes to test the effects of those parameters on the incorporation efficiency of MP in liposomes. PCs with different acyl chain lengths were used as well as another phospholipid (phosphatidylserine) which has a different headgroup. The liposomes were hydrated either at a final concentration of 1 mM or 10 mM. Table 4 shows that in all cases the efficiency of MP incorporation was higher when the liposomes were hydrated at 10 mM final concentration rather than at 1 mM final concentration.

TABLE 4

Effect of lipid composition and the final hydration concentration of liposomes on the incorporation efficiency of MP in liposomes.

| | Incorporation efficiency (%) Final Hydration Concentration of Liposomes | |
|---|---|---|
| Lipid Composition | 1 mM[a] | 10 mM[b] |
| Dilauryl (C12) phosphatidylcholine | 38.1 | 83.0 ± 3.0 |
| Dimyristoyl (C14) phosphatidylcholine | 60.3 | 97.5 ± 2.5 |
| Dipalmitoyl (C16) phosphatidylcholine | 40.3 | 86.5 ± 3.5 |
| Distearoyl (C18:0) phosphatidylcholine | 57.1 | 90.5 ± 2.5 |
| Dioleoyl (C18:1) phosphatidylcholine | 34.9 | 92.5 ± 2.5 |
| Dioleoyl (C18:1) phosphatidylserine | ND | 95.0 ± 2.0 |

[a]The incorporation efficiency values were obtained from one experiment. ND means not determined.
[b]Incorporation efficiencies were reported as the average of two experiments ± error.

When the liposomes were hydrated at 10 mM final concentration, at least 80% MP incorporation was observed with all the lipids tested. This showed that our method of MP incorporation into liposomes was compatible with various lipids.

Among the different lipids tested, DOPC was one of the easiest to handle. Thus it was decided to use the composition of MP/DOPC at a molar ratio of 1/1000 for cell studies. The liposomes were hydrated at a final concentration of 10 mM and sonicated for 15-20 min.

Inhibition by Antisense Oligonucleotide Complementary to the L6 Junction of the bcr-abl Gene Both BV173 and K562 cells bear characteristics of Ph+CML cells. BV173 and K562 contain L6 and K28 junctions, respectively. Antisense oligonucleotides, complementary to the L6 junction of the bcr-abl gene, in the form of MP were used. They were delivered to both BV173 and K562 cells either as liposomal or free oligonucleotides. As shown by FIG. 1, the number of BV173 cells decreased as the concentration of liposomal or free oligonucleotides increased. When 100 and 250 nM of L-MP were used, the number of BV173 cells decreased to 50 and 20 percent of control (untreated cells), respectively. Thus, approximately 50 and 90% growth inhibition of BV173 cells were observed. However, when the same concentrations of free MP were used, the number of BV173 cells remained about 100% of control. Thus, when 100 or 250 nM of free MP were used, there was no growth inhibitory effect on BV173 cells. At 500 nM of L-MP or free MP, over 80% growth inhibition of BV173 cells was observed for both cases. Under identical conditions, there was hardly any growth inhibition of K562 cells even when 500 nM of L-MP or free MP was used. Growth inhibition was not found when empty liposomes were used (data not shown).

Figure 2:
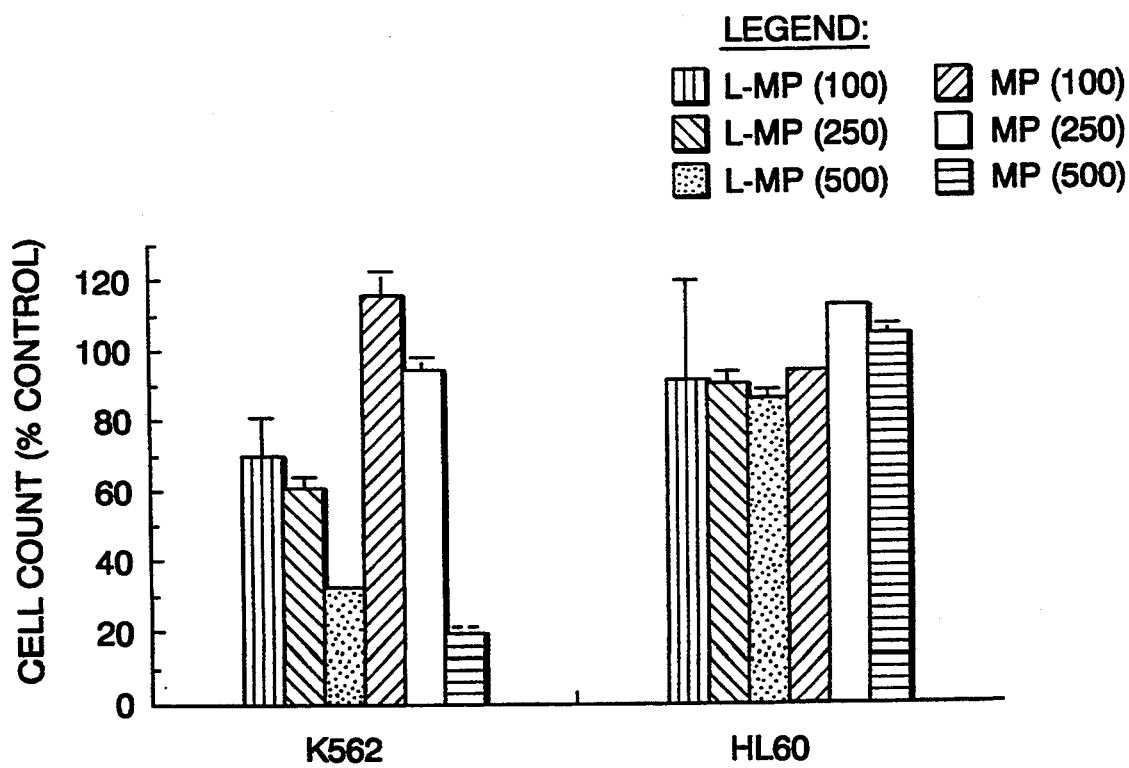
FIG. 2 shows growth inhibition of K562 and HL60 cells by liposomal or free methyl phosphonate complementary to the K28 junction of the bcr-abl fusion gene mRNA. Concentrations of liposomal or free MP used varied between 100 to 500 nM. After 5 days of treatment, the cells were harvested over a 10% Ficoll solution and counted. The number of treated cells were reported as percent of the number of untreated cells. The values were average of two wells±error.

Inhibition by Antisense Oligonucleotides Complementary to the K28 Junction of the bcr-abl Gene Antisense oligos, complementary to the K28 junction of the bcr-abl gene, in the form of MP were used. Antisense oligonucleotides were delivered to both K562 and HL60 cells. K562 cells were Ph+ and HL60 cells were Ph−. Five days after the addition of liposomal or free oligonucleotides, the cells were harvested and counted. The total number of K562 cells decreased to 70, 60 or 35% when 100, 250 or 500 nM of L-MP were used (FIG. 2). This corresponded to approximately 30, 40 and 65% growth inhibition. When free MP was used, the number of K562 cells did not decrease until 500 nM concentration. The number of HL60 cells hardly changed in the presence of L-MP or free MP. Again, empty liposomes did not have any inhibitory effect on the growth of K562 or HL60 cells (data not shown).

Figure 3:
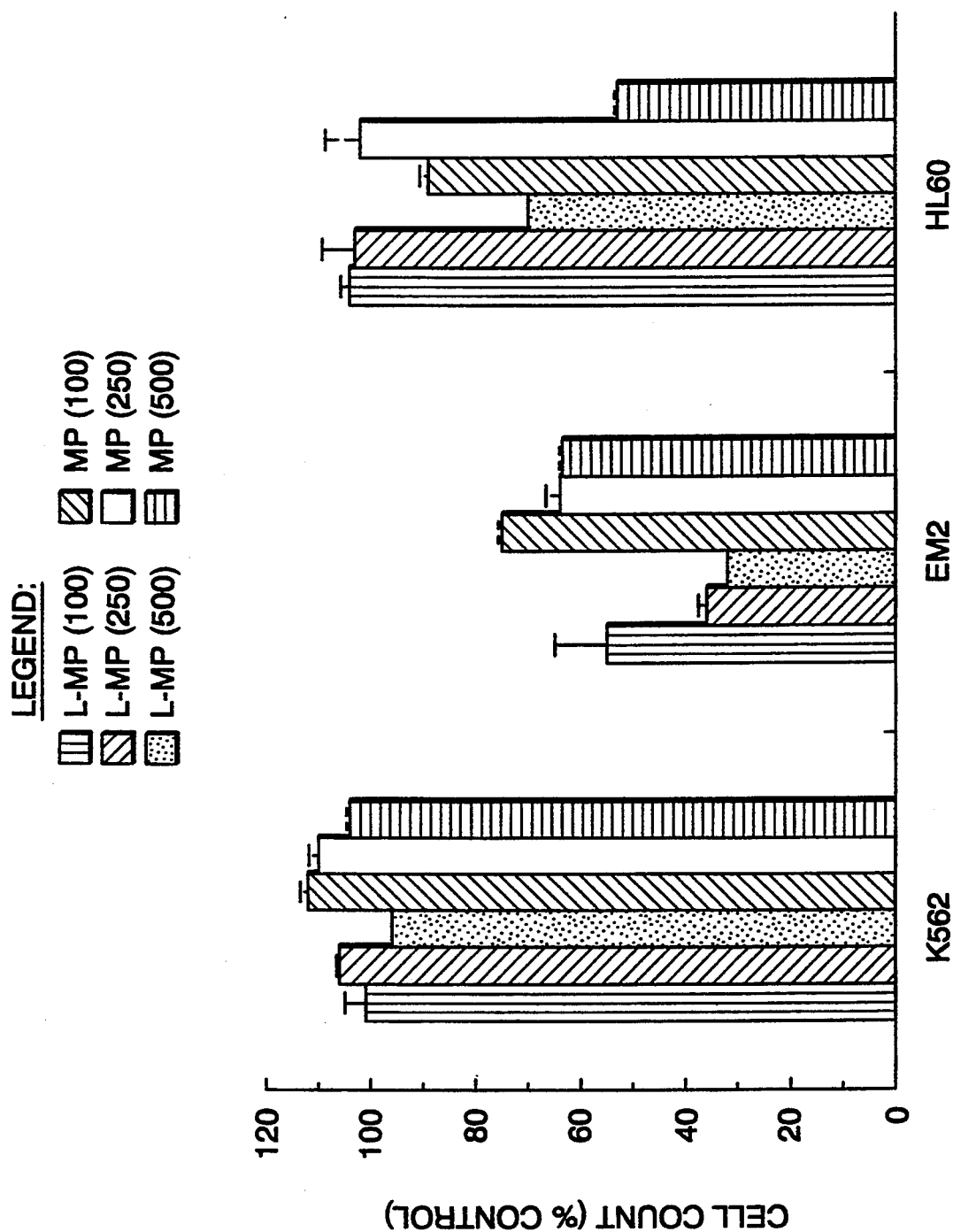
FIG. 3 shows growth inhibition of K562, EM2 and HL60 cells by liposomal or free methyl phosphonate complementary to the translation initiation site of the bcr-abl fusion gene mRNA. Concentrations of liposomal or free MP used varied between 100 to 500 nM. After 5 days of treatment, the cells were harvested over a 10% Ficoll solution and counted. The number of treated cells were reported as percent of the number of untreated cells. The values were average of two wells±error.

Inhibition by Antisense Oligonucleotide Complementary to the Translation Initiation Site of the bcr-abl Gene K562 and EM2 cells are Ph+ CML cells while HL60 cells are not. Antisense oligonucleotides, complementary to the translation initiation site of the bcr-abl gene, in the form of MP were used. Increasing concentrations of L-MP and MP were added to all three different types of cells (FIG. 3). The number of K562 cells was not affected by the presence of L-MP or free MP. However, the number of EM2 cells decreased to 30–60% of control. In other words, 40–70% inhibition was observed. When identical concentrations of free MP were used, the number of EM2 cells decreased to about 70–80% of control, which was interpreted as 20–30% inhibition. Thus, when the same concentrations of L-MP and free MP were added to EM2 cells, greater inhibition effect was observed with L-MP than free MP. The number of HL60 cells did not decrease till 500 nM of L-MP or free MP was used. There was no inhibitory effect of empty liposomes on any of these cell types (data not shown).

The preceding description of specific embodiments of the present invention is not intended to be a complete list of every possible embodiment of the invention. Persons skilled in this field will recognize that modifications can be made to the specific embodiments described here that would be within the scope of the present invention.

We claim:

1. A liposomal methyl phosphonate oligonucleotide composition, comprising:
   a liposome which consists essentially of a phosphatidyl choline; and
   an antisense methyl phosphonate oligonucleotide which is entrapped in the liposome;
   where the molar ratio of phospholipids in the liposome to the methyl phosphonate oligonucleotide entrapped in the liposome is between about 100:1 and about 10,000:1.

2. The composition of claim 1, where the molar ratio of phospholipids in the liposome to the methyl phosphonate oligonucleotide entrapped in the liposome is between about 500:1 and about 5,000:1.

3. The composition of claim 1, where the molar ratio of phospholipids in the liposome to the methyl phosphonate oligonucleotide entrapped in the liposome is about 1,000:1.

4. The composition of claim 1, where the liposome is unilamellar.

5. The composition of claim 1, where the liposome consists essentially of dioleoyl phosphatidyl choline.

6. A method of treating chronic myeloid leukemia, comprising administering to a living mammalian subject in an amount effective to inhibit the growth of leukemic cells an antisense liposomal methyl phosphonate oligonucleotide composition which comprises:
   a liposome which consists essentially of a phosphatidyl choline; and
   an antisense methyl phosphonate oligonucleotide which is entrapped in the liposome;
   where the molar ratio of phospholipids in the liposome to the methyl phosphonate oligonucleotide entrapped in the liposome is between about 100:1 and about 10,000:1.

7. The method of claim 6, where the molar ratio of phospholipids in the liposome to the methyl phosphonate oligonucleotide entrapped in the liposome is between about 500:1 and about 5,000:1.

8. The method of claim 6, where the molar ratio of phospholipids in the liposome to the methyl phosphonate oligonucleotide entrapped in the liposome is about 1,000:1.

9. The method of claim 6, where the liposome is unilamellar.

10. The method of claim 6, where the liposome consists essentially of dioleoyl phosphatidyl choline.

* * * * *